United States Patent
O'Dea et al.

(10) Patent No.: US 12,402,584 B2
(45) Date of Patent: Sep. 2, 2025

(54) CANNABIS PLANT NAMED 'DW-A1

(71) Applicants: Kathleen O'Dea, Santa Fe, NM (US); Eric Baade, Santa Fe, NM (US)

(72) Inventors: Kathleen O'Dea, Santa Fe, NM (US); Eric Baade, Santa Fe, NM (US)

(73) Assignee: Doozer Works, LLC, Santa Fe (MX)

( * ) Notice: Subject to any disclaimer, the term of this patent is extended or adjusted under 35 U.S.C. 154(b) by 113 days.

(21) Appl. No.: 17/664,946

(22) Filed: May 25, 2022

(65) Prior Publication Data

US 2022/0377998 A1 Dec. 1, 2022

Related U.S. Application Data

(60) Provisional application No. 63/193,896, filed on May 27, 2021.

(51) Int. Cl.
*A01H 5/10* (2018.01)
*A01H 6/28* (2018.01)

(52) U.S. Cl.
CPC ............... *A01H 6/28* (2018.05); *A01H 5/10* (2013.01)

(58) Field of Classification Search
None
See application file for complete search history.

(56) References Cited

U.S. PATENT DOCUMENTS

2014/0298511 A1* 10/2014 Lewis .................. A61K 36/185
800/298

OTHER PUBLICATIONS

Hemp Flower, 2020, https://thehempcollect.com/lifter-hemp-flower-review/.*
Darby, 2023, "2022 Hemp Flower Variety Trial", Northwest Crops & Soil Program, University of Vermont Extension, 1-19.*
Saloner et al 2021, Industrial Crops & Products, 167:1-13.*

* cited by examiner

*Primary Examiner* — Jason Deveau Rosen
(74) *Attorney, Agent, or Firm* — Hunt IP Law

(57) ABSTRACT

The unique annual herbaceous *Cannabis* plant variety 'DW-A1' is provided. The variety can be distinguished by its outstanding features of high CBG, virtually undetectable CBD and THC, powdery mildew resistance, sturdy stems for wind-resistance, and being a high terpene producer.

7 Claims, 5 Drawing Sheets
(5 of 5 Drawing Sheet(s) Filed in Color)

CANNABIS PLANT NAMED 'DW-A1

CROSS REFERENCE TO RELATED APPLICATIONS

The present Application for Patent claims priority to Provisional Application No. 63/193,896 entitled "*CANNABIS* PLANT NAMED 'DW-A1'" filed May 27, 2021, which is hereby expressly incorporated by reference herein.

LATIN NAME OF THE GENUS AND SPECIES

Genus—*Cannabis*.
Species—*sativa*.

VARIETY DENOMINATION

The new *Cannabis* plant claimed is of the variety denominated 'DW-A1'.

BACKGROUND OF THE INVENTION

Field of the Invention

The present invention relates to a new and distinct annual variety of *C. sativa*, which has been given the variety denomination of 'DW-A1'. 'DW-A1' is intended for use as a medicinal herb for sale in *Cannabis* dispensaries, hemp farming, high value cannabinoid extraction, and to make products containing CB G. This variety also has value as part of a breeding program to develop improved *Cannabis* varieties.

Background of the Related Art

The genus *Cannabis* has been in use by humans for millennia, due to the multiplicity of its benefits to humans, including the considerable value and utility of its fiber, the nutritional value of its seeds, and the medicinal value of its floral parts and products made from them. Currently, the genus is under intense legal commercialization in the United States as industrial hemp for a variety of purposes including biodegradable plastics and building materials, clothing, paper, food, fuel, and medicines.

Cannabidiol (CBD) extracted from *Cannabis* is widely used in over-the-counter medicines and topical treatments and is also the active ingredient in the FDA-approved drug Epidiolex®. CBD is just one of at least dozens—perhaps hundreds—of cannabinoids endogenous to *Cannabis*, tetrahydrocannabinol (THC) being the other cannabinoid that is most well-known. The cannabinoids as a group interact with the human endocannabinoid receptors, which are distributed in the brain and throughout the body. The study of the endocannabinoid system (ECS) in humans and other mammals is an area of increasing interest and holds tremendous promise for the future of medicine. See, e.g., Russo (2019). Cannabis and Pain, *Pain Medicine*, 20(10): 1; 20(11):2083-2085; and Russo (2016). Clinical Endocannabinoid Deficiency Reconsidered: Current Research Supports the Theory in Migraine, Fibromyalgia, Irritable Bowel, and Other Treatment-Resistant Syndromes, *Cannabis Cannabinoid Res.* 1(1): 154-165.

SUMMARY OF THE INVENTION

The present invention relates to a new and distinct annual variety of *C. sativa*, which has been given the variety denomination of 'DW-A1'. 'DW-A1' is intended for use as medicinal herb for sale in *Cannabis* dispensaries, hemp farming, high value cannabinoid extraction, and to make products containing CBG. This variety also has value as part of a breeding program to develop improved *Cannabis* varieties.

The new *C. sativa* variety is a selection resulting from a new phenotype discovered growing in a cultivated state. This unique and rare variety (strain) was developed and bred from a single unique hemp plant discovered in a hemp field in Manassa, Colorado in 2018. This plant was pollinated by a high CBD plant from which 22 seeds were produced before the end of her lifecycle. Over two years, through crossing, selfing, back-crossing, and crossing again, then testing thousands of seedlings, this variety has been stabilized to produce high CBG, virtually no THC, and high percentages of unique medicinally active terpenes which include myrcene, a-pinene, limonene, b-pinene, beta-caryophyllene, nerolidol, citronellol, and more. Through genetic sequencing by Medicinal Genomics®, 'DW-A1' has been confirmed to carry a double-mutant in the main synthesis pathways of both THC and CBD, explaining the consistent, near-zero levels of THC and CBD.

A sexual reproduction of the new variety in Manassa, Colorado has demonstrated that the new variety reproduces true to type with all of the morphological characteristics, as herein described, firmly fixed and retained through successive generations of such asexual propagation. Chemotypic characteristics of each new variety are variable based upon cultivation conditions, as is typical of *Cannabis* plants. Accordingly, while chemotypic information provided herein is representative of performance of the new varieties under a particular set of cultivation conditions, it is not limiting on other chemotypic profiles obtainable under a different set of cultivation conditions. A stable seed line of each of the new varieties has also been developed by successive generations of interbreeding and selection to correspond to the phenotypic characteristics described herein. A stable seed line of the new variety has also been developed by successive generations of interbreeding and selection to correspond to the phenotypic characteristics described herein.

Analysis of the genome of 'DW-A1' has shown point mutations in the THCA synthase gene, and various deletions in the CB DA synthase gene. Such mutations are likely why the variety accumulates high CBG.

The following characteristics of the new variety have been repeatedly observed and can be used to distinguish 'DW-A1' as a new and distinct variety of *C. sativa* plant:
1. High CBG
2. Virtually undetectable CBD and THC (has tested at 8% CBGA, 0.9% CBDA and non-detectable THC).
3. Powdery Mildew Resistant
4. Early to mid-season finish
5. Hybrid indica-dominant phenotype
6. Thick, sturdy stems for wind-resistance
7. High germination rate >98%
8. Super rapid and vigorous growth out of the husk
9. High terpene producer

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying photographic illustrations show the typical appearance of the new variety 'DW-A1'. The colors are as nearly true as is reasonably possible in a color representation of this type. Colors in the photographs may differ slightly from the color values cited in the detailed botanical description which accurately describes the colors of the new plant.

DETAILED DESCRIPTION

Figure 1:
FIG. 1 is a photograph of the inflorescence of the new variety 'DW-A1'.
Figure 2:
FIG. 2 is a photograph of the inflorescence of the new variety 'DW-A1'.
Figure 3:
FIG. 3 is a photograph of a young plant of the new variety 'DW-A1'
Figure 4:
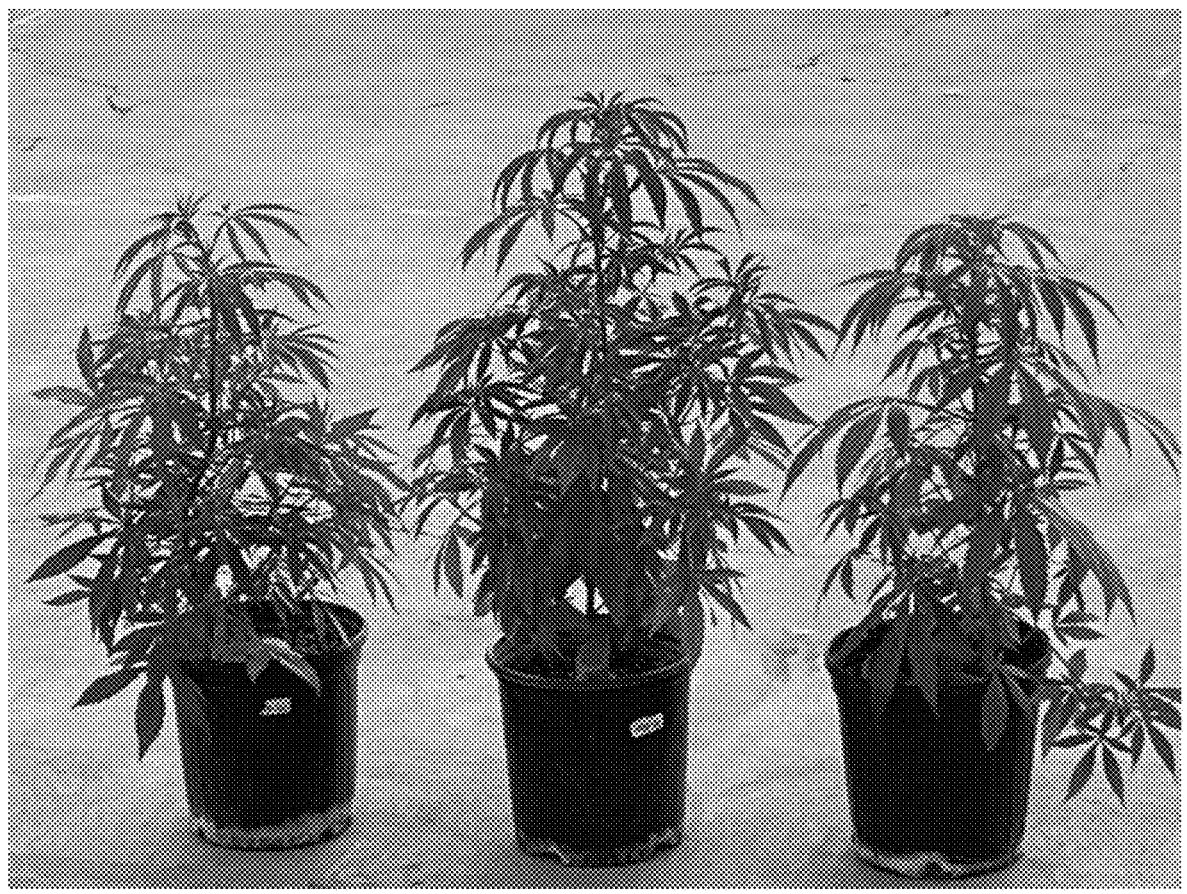
FIG. 4 is a photograph of the whole plant of the new variety 'DW-A1'.
Figure 5:
FIG. 5 is a photograph of a close up of the flower of the new variety 'DW-A1'.

Some embodiments of the invention relate to a seed from a *Cannabis* plant designated 'DW-A1' wherein a representative sample of seed of said plant has been deposited under NCIMB 44620 on Jun. 30, 2025, at National Collections of Industrial, Food and Marine Bacteria (NCIMB) Ltd. Located at Wellheads Place, Aberdeen, Dyce. AB21 7GB Scotland. Upon issuance of a patent, all restrictions imposed by the depositor on the availability to the public of the deposited material will be irrevocably removed, and the deposit is intended to meet all the requirements of 37 C.F.R. §§ 1.801-1.809. The deposit has been accepted under the Budapest Treaty and will be maintained in the depository for a period of 30 years, 5 years after the last request, or the effective life of the patent, whichever is longer, and will be replaced if necessary during that period.

Some embodiments of the invention relate to a *Cannabis* plant, or plant part, tissue, or cell thereof produced by growing the seed of 'DW-A1', or a descendant thereof. Plant parts can include the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like.

The plants, or plant parts of the invention can display a cannabinoid profile within the ranges set forth in Table 1, as defined herein. The productivity of any given cannabinoid and/or the amounts or ratios of cannabinoids, terpenes, and other plant products can be, by nature, quite variable. The variability can be contributed to by weather, latitude, soil and feeding conditions, pathogens, and numerous other agronomic, horticultural, and biological factors.

Some embodiments of the invention relate to methods of using the plant in a breeding program to produce *Cannabis* progeny including a cannabinoid profile generally within the ranges as set forth in Table 1. Details of existing *Cannabis* plant varieties and breeding are described in Potter et al. (2011, *World Wide Weed: Global Trends in Cannabis Cultivation and Its Control*); Holland (2010, *The Pot Book: A Complete Guide to Cannabis*, Inner Traditions/Bear & Co, ISBN 1594778981, 9781594 778988); Green I (2009, *The Cannabis Grow Bible: The Definitive Guide to Growing Marijuana for Recreational and Medical Use*, Green Candy Press, 2009, ISBN 1931160589, 9781931160582); Green II (2005, *The Cannabis Breeder's Bible: The Definitive Guide to Marijuana Genetics, Cannabis Botany and Creating Strains for the Seed Market*, Green Candy Press, 1931160279, 9781931160278); Starks (1990, *Marijuana Chemistry Genetics, Processing & Potency*, ISBN 0914171399, 9780914171393); Clarke (1981, *Marijuana Botany, an Advanced Study: The Propagation and Breeding of Distinctive Cannabis*, Ronin Publishing, ISBN 091417178X, 9780914171782); Short (2004, *Cultivating Exceptional Cannabis: An Expert Breeder Shares His Secrets*, ISBN 1936807122, 9781936807123); Cervantes (2004, *Marijuana Horticulture: The Indoor/Outdoor Medical Grower's Bible*, Van Patten Publishing, ISBN 187882323X, 9781878823236); Franck et al. (1990, *Marijuana Grower's Guide*, Red Eye Press, ISBN 0929349016, 9780929349015); Grotenhermen and Russo (2002, *Cannabis and Cannabinoids: Pharmacology, Toxicology, and Therapeutic Potential*, Psychology Press, ISBN 0789015080, 9780789015082); Rosenthal (2007, *The Big Book of Buds: More Marijuana Varieties from the World's Great Seed Breeders*, ISBN 1936807068, 9781936807062); Clarke, RC (*Cannabis: Evolution and Ethnobotany* 2013); King, J (*Cannabible* Vols 1-3, 2001-2006); and four volumes of Rosenthal's *Big Book of Buds* series (2001, 2004, 2007, and 2011), each of which is herein incorporated by reference in its entirety for all purposes.

The present invention also relates to variants, mutants, and minor modifications of the seeds, plant parts, and/or whole plants of the *Cannabis* plants of the present invention. Variants, mutants, and minor modifications of the seeds, plants, plant parts, and plant cells of the present invention can be generated by methods well known and available to one skilled in the art, including but not limited to, mutagenesis (e.g., chemical mutagenesis, radiation mutagenesis, transposon mutagenesis, insertional mutagenesis, signature tagged mutagenesis, site-directed mutagenesis, and natural mutagenesis), knock-outs/knock-ins, antisense, and RNA interference. For more information about mutagenesis in plants, such as agents or protocols, see Acquaah et al. (*Principles of plant genetics and breeding*, Wiley-Blackwell, 2007, ISBN 1405136464, 9781405136464) which is herein incorporated by reference in its entirety. Other kinds of modifications practiced in the *Cannabis* industry, including but not limited to feminization of seeds and/or daylength neutrality/autoflowering, are also within the scope of the invention and are within the level of skill in the art to execute.

The present invention also relates to a mutagenized population of the *Cannabis* plants of the present invention, and methods of using such populations. In some embodiments, the mutagenized population can be used in screening for new *Cannabis* lines which comprises one or more or all of the morphological, physiological, biological, and/or chemical characteristics of *Cannabis* plants of the present invention.

In some embodiments, the new *Cannabis* plants obtained from the screening process comprise one or more or all of the morphological, physiological, biological, and/or chemical characteristics of *Cannabis* plants of the present invention, and one or more additional or different new morphological, physiological, biological, and/or chemical characteristic.

The present invention also provides any compositions or any products made from or isolated from the plants of the present invention. In some embodiments, the compositions/products comprise an extract of the plants. In some embodiments, the extract can contain a higher percentage of terpenes/terpenoids compared to extract isolated from a control *Cannabis* plant variety (e.g., an existing variety, such as a recreational *Cannabis* plant variety). In some embodiments, the invention relates to a smokable or edible product comprising the *Cannabis* plant, or plant part, tissue, cell, extract, or isolate.

The present invention provides methods of using the *Cannabis* plants or any parts, any compositions, or any chemicals derived from said plants of the present invention.

In some embodiments, the plants of the present invention can be used to produce new plant varieties. In some embodiments, the plants are used to develop new varieties or hybrids with desired phenotypes or genotypes.

In some embodiments, selection methods, e.g., molecular marker assisted selection, can be combined with breeding methods to accelerate the process. Additional breeding methods known to those of ordinary skill in the art include, e.g., methods discussed in Chahal and Gosal (*Principles and procedures of plant breeding: biotechnological and conventional approaches*, CRC Press, 2002, ISBN 084931321X, 9780849313219); Taji et al. (*In vitro plant breeding*, Routledge, 2002, ISBN 156022908X, 9781560229087); Richards (*Plant breeding systems*, Taylor & Francis US, 1997, ISBN 0412574500, 9780412574504); Hayes (*Methods of Plant Breeding*, Publisher: READ BOOKS, 2007, ISBN 1406737062, 9781406737066); each of which is incorporated by reference in its entirety. The *Cannabis* genome has been sequenced (Bakel et al., The draft genome and transcriptome of *Cannabis sativa*, *Genome Biology*, 12(10):R102, 2011). Molecular makers for *Cannabis* plants are described in Datwyler et al. (Genetic variation in hemp and marijuana (*Cannabis sativa* L.) according to amplified fragment length polymorphisms, *J Forensic Sci.* 2006 March; 51(2):371-5); Pinarkara et al., (RAPD analysis of seized marijuana (*Cannabis sativa* L.) in Turkey, *Electronic Journal of Biotechnology*, 12(1), 2009), Hakki et al., (Inter simple sequence repeats separate efficiently hemp from marijuana (*Cannabis sativa* L.), *Electronic Journal of Biotechnology*, 10(4), 2007); Gilmore et al. (Isolation of microsatellite markers in *Cannabis sativa* L. (marijuana), *Molecular Ecology Notes*, 3(1): 105-107, March 2003); Pacifico et al., (Genetics and marker assisted selection of chemotype in *Cannabis sativa* L.), *Molecular Breeding* (2006) 17:257-268); and Mendoza et al., (Genetic individualization of *Cannabis sativa* by a short tandem repeat multiplex system, *Anal Bioanal Chem* (2009) 393:719-726); each of which is herein incorporated by reference in its entirety.

In some embodiments, the *Cannabis* plant, or plant part, tissue, or cell of 'DW-A1' comprises a cannabinoid profile as set forth in Table 1 and a terpene profile as set forth in Table 2. Due to the natural variability of chemotypic expression that is commonly observed in *Cannabis* plants, arising from numerous causes as discussed above, the values set forth in Tables 1 and 2 do not reflect the only possible range of outcomes that can be obtained from plants of the new variety. Thus, these values are merely exemplary of observed values (middle column) and predicted normal variations from the observed values. Variations outside these ranges are also within the scope of the invention.

TABLE 1

Exemplary Profiles of Key Cannabinoids.

| Cannabinoid | Percent | Percent | Percent | Percent | Percent |
|---|---|---|---|---|---|
| THCa | 0.0075 | 0.01 | 0.02 | 0.03 | 0.0375 |
| Delta 9 THC | 0.0075 | 0.01 | 0.01 | 0.01 | 0.0125 |
| Delta 8 THC | 0.00 | 0.0025 | 0.005 | 0.01 | 0.0125 |
| CBDa | 0.0075 | 0.01 | 0.065 | 0.12 | 0.15 |
| CBD | 0.0075 | 0.01 | 0.01 | 0.01 | 0.0125 |
| CBDVa | 0.0075 | 0.01 | 0.01 | 0.01 | 0.0125 |

TABLE 1-continued

Exemplary Profiles of Key Cannabinoids.

| Cannabinoid | Percent | Percent | Percent | Percent | Percent |
|---|---|---|---|---|---|
| CBN | 0.0075 | 0.01 | 0.01 | 0.01 | 0.0125 |
| CBGa | 8.235 | 10.98 | 11.78 | 12.58 | 15.725 |
| Total Cannabinoids * | 8.325 | 11.1 | 11.855 | 12.61 | 15.7625 |

* Total Cannabinoids = Total THC + Total CBD + Total CBG + Total THCV + Total CBC + Total CBDV + Δ8THC + CBL + CBN

TABLE 2

Exemplary Profiles of Key Terpenes (% by dry weight)

| Terpene | Percent | Percent | Percent | Percent | Percent |
|---|---|---|---|---|---|
| Myrcene | 0.445 | 0.89 | 1.05 | 1.21 | 1.815 |
| Alpha pinene | 0.2575 | 0.515 | 0.6175 | 0.72 | 1.08 |
| Limonene | 0.1475 | 0.295 | 0.3025 | 0.31 | 0.465 |
| Beta pinene | 0.0425 | 0.085 | 0.2275 | 0.37 | 0.555 |
| B-Caryophyllene | 0.04 | 0.08 | 0.06 | 0.04 | 0.06 |
| Nerolidol | 0.035 | 0.07 | 0.055 | 0.04 | 0.06 |
| Humulene | 0.02 | 0.04 | 0.08 | 0.12 | 0.18 |
| Linalool | 0.005 | 0.01 | 0.14 | 0.27 | 0.405 |
| Bisabool | 0.01 | 0.02 | 0.05 | 0.08 | 0.12 |

In some embodiments, the invention relates to a *Cannabis* clone regenerated from the *Cannabis* plant, plant part, tissue, cell, or seed of 'DW-A1' wherein the plant is a clonal descendent.

In some embodiments, the invention relates to a method of producing an FI *Cannabis* seed, wherein the method includes crossing the plant with a different *Cannabis* plant and harvesting the resultant FI *Cannabis* seed. In some embodiments, the invention relates to the F1 hybrid *Cannabis* seed produced by this method. In some embodiments, the invention relates to a FI hybrid *Cannabis* plant produced by growing the FI hybrid *Cannabis* seed. In some embodiments, the invention relates to a *Cannabis* clone regenerated from the FI hybrid *Cannabis* plant. In some embodiments, the invention relates to a smokable or edible product comprising *Cannabis* tissue from the FI hybrid *Cannabis* plant.

In some embodiments the invention relates to seed line from a clonally propagated plant of the new variety. In some embodiments, the seed line is that of the deposited seed recited herein. In other embodiments, the seed line is one that is separately established through interbreeding and selection of plants of the new variety, using pollen from reversed females of the new variety and/or from relatives/ancestors of the new variety. In these embodiments, crosses and selections are conducted through successive generations to obtain a line of seed that stably produces progeny having physical and chemical properties within the ranges recited herein for the new variety. In some embodiments, this seed line is feminized seed, having been feminized using techniques known to those of skill in the art.

What is claimed is:

1. A seed or plant of a *Cannabis* plant designated 'DW-A1' wherein a representative sample of seed of said plant has been deposited under NCIMB 44620; wherein flower produced from the *Cannabis* plant comprises a cannabinoid profile of:
   0.0075-0.0375% THCa;
   0.0075-0.0125% Delta 9 THC;
   0.00-0.0125% Delta 8 THC;
   0.0075-0.15% CBDa; and
   0.0075-0.0125% CBD.

2. A *Cannabis* plant, or plant part, tissue, or cell thereof produced by growing the seed of claim 1, or a clonal descendant thereof, wherein flower produced from the *Cannabis* plant comprises a cannabinoid profile of:
- 0.0075-0.0375% THCa;
- 0.0075-0.0125% Delta 9 THC;
- 0.00-0.0125% Delta 8 THC;
- 0.0075-0.15% CBDa; and
- 0.0075-0.0125% CBD.

3. The *Cannabis* plant, or plant part, tissue, or cell thereof of claim 2 comprising a cannabinoid profile of:
- 0.01-0.03% THCa;
- 0.01% Delta 9 THC;
- 0.0025-0.01% Delta 8 THC;
- 0.01-0.012% CBDa;
- 0.01% CBD; and
- 8.235-15.7625% CBGa.

4. The *Cannabis* plant part of claim 2, wherein said plant part is selected from the group consisting of: stems, trichomes, leaves, and flower buds.

5. A method of breeding a *Cannabis* plant comprising the steps of:
- providing a first *Cannabis* plant selected from:
  - a. a *Cannabis* plant designated 'DW-A1' wherein a representative sample of seed of said plant has been deposited under NCIMB 44620; or
  - b. a clonal descendant of the *Cannabis* plant designated 'DW-A1'; crossing the first *Cannabis* plant with a second *Cannabis* plant;
- selecting progeny from the cross as an F1 generation; and
- utilizing the F1 generation for at least one of cultivation, flower production, seed production, or further breeding.

6. The method of claim 5, wherein the second *Cannabis* plant is a *Cannabis* plant designated 'DW-A1' and wherein flower from the F1 generation from the selecting step comprises a cannabinoid profile of:
- 0.0075-0.0375% THCa;
- 0.0075-0.0125% Delta 9 THC;
- 0.00-0.0125% Delta 8 THC;
- 0.0075-0.15% CBDa;
- 0.0075-0.0125% CBD; and
- 8.235-15.7625% CBGa.

7. The method of claim 5, wherein the second *Cannabis* plant is not a *Cannabis* plant designated 'DW-A1', further comprising the steps of:
- crossing a *Cannabis* plant from the F1 generation with another *Cannabis* plant that is either (i) a plant from the F1 generation or (ii) a *Cannabis* plant designated 'DW-A1', to produce an F2 generation; and
- selecting progeny from the F2 generation, where flower from any selected progeny comprises a cannabinoid profile of at least:
  - (a) 0.0075-0.0375% THCa;
    - 0.0075-0.0125% Delta 9 THC; and
    - 0.00-0.0125% Delta 8 THC;
  - or
  - (b) 0.0075-0.15% CBDa; and
    - 0.0075-0.0125% CBD;
  - or both (a) and (b).

* * * * *